United States Patent
Hulko et al.

(10) Patent No.: US 9,157,115 B2
(45) Date of Patent: Oct. 13, 2015

(54) APTAMER SENSOR DEVICE

(71) Applicant: Sony Corporation, Minato-ku (JP)

(72) Inventors: Michael Hulko, Stuttgart (DE);
Nadejda Krasteva, Stuttgart (DE);
Ingeborg Hospach, Stuttgart (DE);
Gabriele Nelles, Stuttgart (DE)

(73) Assignee: SONY Corporation, Tokyo (JP)

( * ) Notice: Subject to any disclaimer, the term of this patent is extended or adjusted under 35 U.S.C. 154(b) by 94 days.

(21) Appl. No.: 13/961,407

(22) Filed: Aug. 7, 2013

(65) Prior Publication Data
US 2014/0051090 A1    Feb. 20, 2014

(30) Foreign Application Priority Data

Aug. 14, 2012 (EP) .................................... 12180409

(51) Int. Cl.
| | |
|---|---|
| C07H 21/02 | (2006.01) |
| C07H 21/04 | (2006.01) |
| A61K 48/00 | (2006.01) |
| C12Q 1/68 | (2006.01) |
| G01N 33/53 | (2006.01) |
| G01N 33/542 | (2006.01) |

(52) U.S. Cl.
CPC .......... *C12Q 1/6834* (2013.01); *G01N 33/5308* (2013.01); *G01N 33/542* (2013.01); *G01N 2333/9005* (2013.01)

(58) Field of Classification Search
CPC ............................... C12N 15/113; A61K 48/00
See application file for complete search history.

(56) References Cited

U.S. PATENT DOCUMENTS 8,962,238 B2 * 2/2015 Todd et al. ..................... 435/6.1

OTHER PUBLICATIONS

David H. J. Bunka, et al., "Aptamers come of age—at last", Nature Rev. Microbiol., vol. 4, Aug. 2006, pp. 588-596.
S. Tombelli, et al., "Analytical applications of aptamers", Biosensors and Bioelectronics, vol. 20, 2005, pp. 2424-2434.
Ted Chu, et al., "Using aptamers to identify and enter cells", Current Opinion in Molecular Therapeutics, vol. 9, 2007, pp. 137-144.
Justin P. Gallivan, "Toward reprogramming bacteria with small molecules and RNA", Current Opinion in Chemical Biology, vol. 11, 2007, pp. 612-619.
Rebecca K. Montange, et al., "Riboswitches: Emerging Themes in RNA Structure and Function", Annu. Rev. Biophys., vol. 37, 2008, pp. 117-133.

* cited by examiner

*Primary Examiner* — Amy Bowman
(74) *Attorney, Agent, or Firm* — Oblon, McClelland, Maier & Neustadt,, L.L.P.

(57) ABSTRACT

The present invention relates to aptazyme sensor devices comprising, in addition to the aptamer, ribozyme and communication components, a competitive inhibitory component with a metal nanoparticle or a competitive inhibitory and signalling component with a metal nanoparticle and a label, such that the enzymatic activity of the ribozyme is inhibited as long as the inhibitory or the inhibitory and signalling component is bound to the substrate binding site of the ribozyme. The aptazyme sensor devices of the invention have increased shelf-life and are suitable for the parallel detection of different ligands by using an array of aptazyme sensor devices utilizing inhibitory and inhibitory and signalling components with different metal nanoparticles. The present invention furthermore relates to the post-synthetic chemical modification of the aptamer component for avoiding unspecific binding.

25 Claims, 4 Drawing Sheets

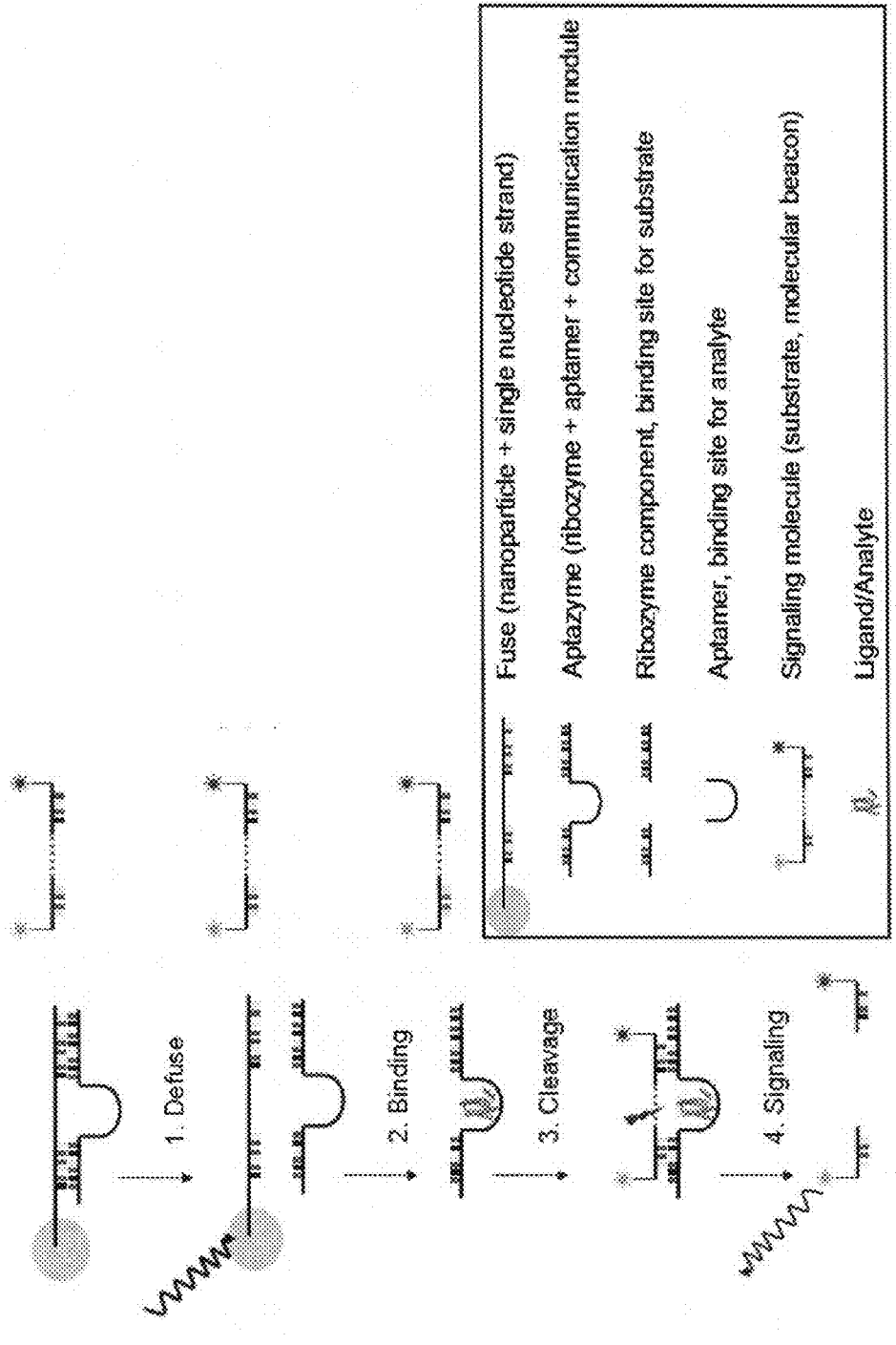

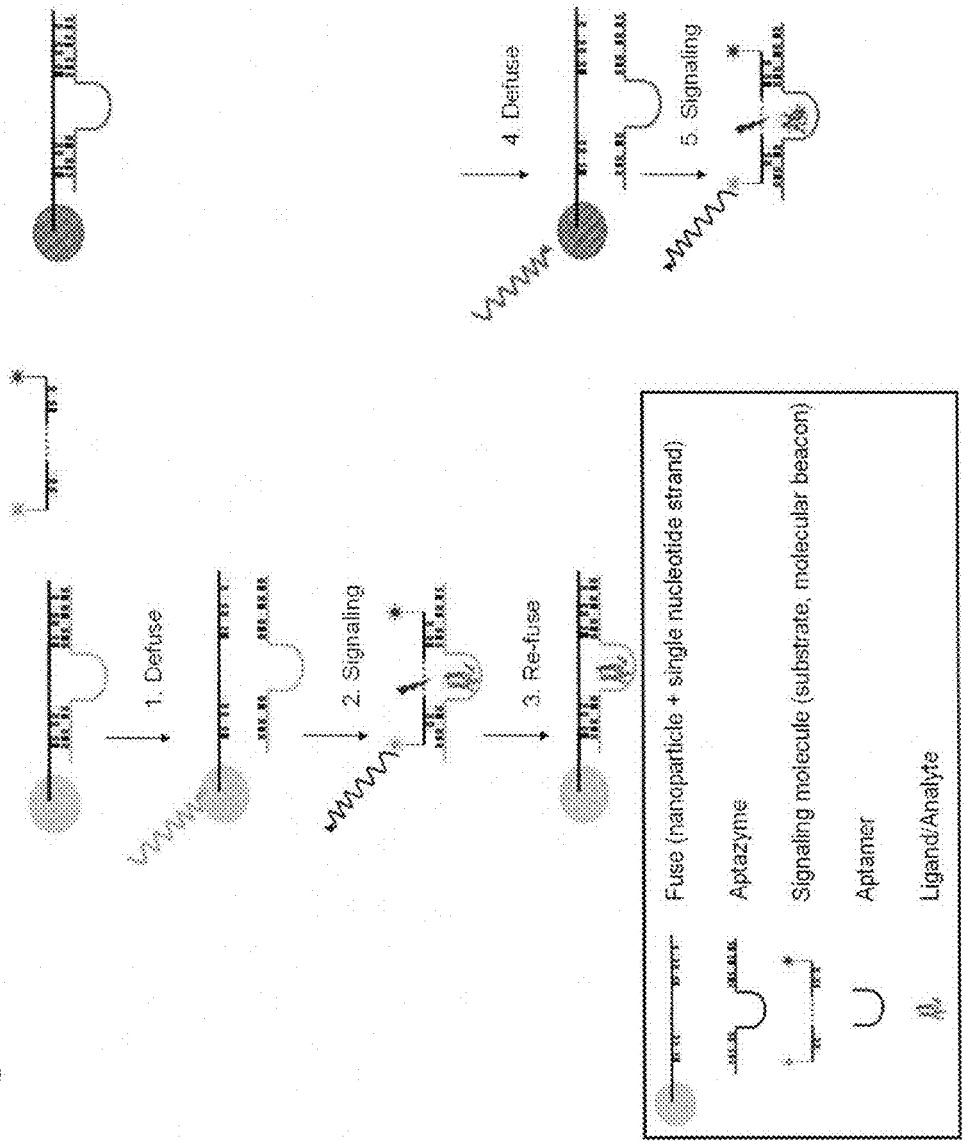

APTAMER SENSOR DEVICE

The present disclosure relates to aptazyme sensor devices comprising, in addition to the aptamer, ribozyme and communication components, a competitive inhibitory component with a metal nanoparticle or a competitive inhibitory and signalling component with a metal nanoparticle and a label, such that the enzymatic activity of the ribozyme is inhibited as long as the inhibitory or the inhibitory and signalling component is bound to the substrate binding site of the ribozyme. The aptazyme sensor devices of the disclosure have increased shelf-life and are suitable for the parallel detection of different ligands by using an array of aptazyme sensor devices utilizing inhibitory components and inhibitory and signalling components with different metal nanoparticles. The present disclosure furthermore relates to the post-synthetic chemical modification of the aptamer component for avoiding unspecific binding.

BACKGROUND OF THE DISCLOSURE

Nucleic acid binding species (aptamers) have emerged as a powerful tool for molecular recognition, and have begun to be widely adapted as biosensors, in drug-delivery systems, and as regulatory elements that control gene expression [1]-[4]. Naturally occurring nucleic acid regulatory elements, riboswitches, have been discovered in a variety of organisms and control the expression of a wide range of genes [5].

One of the major advantages of aptamers over their protein counterparts is that they can be easily coupled to other functional RNAs based largely on secondary structural considerations in order to generate allosteric constructs. To a large extent aptamer-based biosensors (both in vitro and in vivo) can be classified into two major categories: (i) those in which the aptamer binding influences the hybridization state of other nucleic acids and (ii) those in which aptamer binding influences the catalysis of a ribozyme. These allosteric ribozymes derived from aptamers are also known as aptazymes.

Aptamers are nucleic acids that bind their cognate ligands (ranging from metal ions to small molecules to proteins) specifically and tightly. Through rational design and/or directed evolution, aptamers can be engineered into allosteric nucleic acids whose conformations can be regulated by their ligands. Aptamer beacons, aptazymes, and riboswitches all undergo ligand-dependent conformational changes, and have been adapted to signal the concentration of their ligands.

Nucleic acid sensor elements are proving increasingly useful in biotechnology and biomedical applications. A number of ligand-sensing, conformational-switching ribozymes, also known as allosteric ribozymes or aptazymes, have been generated by combination of directed evolution or rational design. Such sensor elements typically fuse a molecular recognition domain (aptamer) with a catalytic signal generator (ribozyme), typically connected to each other via a communication module (single or double strand RNA or DNA).

However, a problem of the highly sensitive aptazyme sensors is that increased sensitivity is accompanied by residual background activity that is detrimental for shelf-life and therefore an obstacle to commercial use.

There is further a need in the art for overcoming the limitation of parallelization of a sensor reaction in a single reaction vessel.

Furthermore, aptamer probes binding unspecifically to surfaces is a widespread problem and reduces sensor performance by leading to false positive results and decreasing sensor sensitivity.

The present disclosure aims to provide improved aptazyme sensors which overcome the limitations of the known aptazyme sensors and which allow sensitive and parallel detection of ligands.

It is a further objective of the present disclosure to provide uses and methods for detecting ligands or analytes in samples as well as for detecting different ligands or analytes in samples.

SUMMARY OF THE DISCLOSURE

According to the present disclosure this object is solved by an aptazyme sensor device for detecting a ligand wherein the device comprises the following three components
(a) an aptamer component, which comprises a binding site for a ligand,
(b) a ribozyme component having a substrate binding site, wherein said ribozyme component has an enzymatic activity towards a substrate, which enzymatic activity can be switched on and off, and which, if switched on, results in generation of a signal upon exposure of the ribozyme component to the substrate and upon binding of the substrate to the substrate binding site,
(c) a communication component, which is a single or double stranded nucleic acid and links (a) to (b) and translates changes in the binding state of component (a) to component (b), wherein (a), (b) and (c) are covalently bound, and which furthermore comprises
(d) an inhibitory component, which comprises a single nucleotide strand covalently bound to a metal nanoparticle, wherein the single nucleotide strand specifically and selectively binds to the substrate binding site of component (b) such that the enzymatic activity in (b) is inhibited,
wherein binding of the single nucleotide strand to the substrate binding site of component (b) is selectively interrupted after exciting plasmon resonance of the metal nanoparticle by irradiation of said metal nanoparticle with light, wherein the enzymatic activity of component (b) is switched on when
(i) a ligand is bound to component (a) and
(ii) the inhibitory component (d) is not bound to component (b).

According to the present disclosure this object is furthermore solved by an array of aptazyme sensor devices for detecting different ligands comprising in one reaction vessel
(i) a substrate with a label
(ii) at least two aptazyme sensor devices according to the disclosure, wherein each aptazyme sensor device comprises a different aptamer component (a) comprising a binding site for a different ligand, and an inhibitory component (d) comprising a different metal nanoparticle,
such that, for each aptazyme sensor device and depending on the metal nanoparticle comprised, the binding of the inhibitory component (d) to component (b) is selectively interrupted by irradiation with light of a specific different wavelength.

According to the present disclosure this object is furthermore solved by another aptazyme sensor device which comprises the following three components
(a) an aptamer component, which comprises a binding site for a ligand,
(b) a ribozyme component having a substrate binding site, wherein said ribozyme component has an enzymatic activity towards a substrate, which enzymatic activity can be switched on and off,
(c) a communication component, which is a single or double stranded nucleic acid and links (a) to (b) and translates changes in the binding state of component (a) to component (b), wherein (a), (b) and (c) are covalently bound, which furthermore comprises
(e) an inhibitory and signalling component, which comprises a single nucleotide strand having a ribozyme cleavage site and which has covalently bound a metal nanoparticle near or at the 5' end and a label near or at the 3' end, or vice versa, wherein the single nucleotide strand binds to the substrate binding site of component (b) such that the enzymatic activity is inhibited,
wherein after binding of the ligand to component (a) the enzymatic activity of component (b) is turned on and results in cleavage of the single nucleotide strand of component (e) at the cleavage site, but wherein no detectable signal is generated from the label,
and wherein, after exciting the plasmon resonance of the metal nanoparticle by irradiation with light, binding of the cleaved component (e) to component (b) is selectively interrupted such that the detectable signal is generated from the label.

According to the present disclosure this object is furthermore solved by an array of aptazyme sensor devices for detecting different ligands comprising in one reaction vessel at least two aptazyme sensor devices according to the disclosure,
wherein each aptazyme sensor device comprises a different aptamer component (a) comprising a binding site for a different ligand, and an inhibitory and signalling component (e) comprising a different metal nanoparticle,
such that, for each aptazyme sensor device and depending on the metal nanoparticle comprised, the binding of the cleaved component (e) to component (b) is selectively interrupted and detectable signal is generated by irradiation with light of a specific different wavelength.

According to the present disclosure this object is furthermore solved by the use of an aptazyme sensor device according to the disclosure for detecting a ligand in a sample.

According to the present disclosure this object is furthermore solved by the use of an array of aptazyme sensor devices according to the disclosure for detecting different ligands in a sample.

According to the present disclosure this object is furthermore solved by the use of an aptazyme sensor device according to the disclosure for reducing unspecific binding properties of component (a).

According to the present disclosure this object is furthermore solved by a method of detecting a ligand in a sample, wherein such method comprises
(i) providing a sample,
(ii) providing an aptazyme sensor device according to the disclosure and a substrate with a label, if applicable,
(iii) contacting said sample with said aptazyme sensor device,
(iv) irradiating the sample with said aptazyme sensor device with light of the wavelength which excites plasmon resonance of the metal nanoparticle of component (d) or (e) of the aptazyme sensor device,
(v) detecting a signal.

According to the present disclosure this object is furthermore solved by a method of detecting different ligands in a sample, wherein such method comprises
(i) providing a sample,
(ii) providing an array of aptazyme sensor devices according to the disclosure,
(iii) contacting said sample with said array of aptazyme sensor devices,
(iv) irradiating the sample with said array of aptazyme sensor devices with light of the wavelength which excites plasmon resonance of one type of metal nanoparticle of component (d) or (e) of the aptazyme sensor devices of said array,
(v) detecting a signal,
(vi) repeating steps (iv) and (v) depending on the number of different metal nanoparticles of said array of aptazyme sensor devices.

DESCRIPTION OF THE PREFERRED EMBODIMENTS OF THE DISCLOSURE

Before the present disclosure is described in more detail below, it is to be understood that this disclosure is not limited to the particular methodology, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art. For the purpose of the present disclosure, all references cited herein are incorporated by reference in their entireties.

Aptazyme Sensor Devices for Detecting Ligands

As described above, the present disclosure provides aptazyme sensor devices.

Such an aptazyme sensor device according to the disclosure comprises the following three components of an aptazyme:
(a) an aptamer component,
(b) a ribozyme component, and
(c) a communication component.

Aptamer Component (a)

Aptamers are oligonucleic acid molecules that bind to a specific target molecule (a ligand). Aptamers are usually created by selecting them from a large random sequence pool, but natural aptamers also exist in riboswitches. Aptamers can be used for both basic research and clinical purposes as macromolecular drugs. Aptamers can be combined with ribozymes to self-cleave in the presence of their target molecule.

More specifically, aptamers can be classified as DNA or RNA aptamers. They consist of (usually short) strands of oligonucleotides.

An aptamer of component (a) of the disclosure is a nucleic acid that binds its ligand specifically and tightly. In embodiments, through rational design and/or directed evolution, the aptamer is engineered into an [allosteric] nucleic acid whose conformation can be regulated by its ligand. In one embodiment, the aptamer is selected out of a library by affinity/binding tests. It undergoes ligand-dependent conformational changes, which will be translated through component (c) to component (b) such that the presence of its ligand can be detected.

The component (a) comprises a binding site for a ligand or analyte to be detected.

The ligand or analyte, whose presence is to be detected, can be any substance like for example a metal ion, small molecule compounds, biopolymers, such as protein, nucleic acids, lipids and the like.

Upon binding of the ligand, component (a) undergoes conformational changes.

Component (a) preferably comprises RNA, DNA, or combinations thereof.

In one embodiment, component (a) is incorporated in component (b) and is flanked at either end by parts of components (c) and (b).

Ribozyme Component (b)

A ribozyme (from ribonucleic acid enzyme, also called RNA enzyme or catalytic RNA) is an RNA molecule possessing a well defined tertiary structure that enables it to catalyze a chemical reaction. Many natural ribozymes catalyze either the hydrolysis of one of their own phosphodiester bonds, or the hydrolysis of bonds in other RNAs, but they have also been found to catalyze the aminotransferase activity of the ribosome. A ribozyme could be for example a so called hairpin or hammer head ribozyme. A ribozyme can also catalyse a reaction at a multiple turnover. In conjunction with embodiments of the present disclosure, in particular with embodiments of aptazyme sensor devices according to the present disclosure this allows for a signal amplification.

Component (b) of the disclosure has a substrate binding site.

In accordance with embodiments of present disclosure, component (b) of the disclosure furthermore has an enzymatic activity towards a substrate which enzymatic activity can be switched on and off, and which, if switched on, results in generation of a detectable signal upon exposure of component (b) to the substrate and upon binding of the substrate to the substrate binding site, wherein the enzymatic activity of component (b) is switched on only when (i) a ligand is bound to component (a) and (ii) the inhibitory component (d) is not bound to component (b).

The enzymatic activity of component (b) is turned/switched on when ligand is bound to component (a) and when no inhibitory component is bound to the substrate binding site, such as the inhibitory component (d).

Communication Component (c)

In embodiments of the present disclosure, the communication component (c) is a single or double stranded nucleic acid that connects/couples component (a) with component (b). It furthermore translates the changes in the binding state of component (a) to component (b), the conformational changes that component (a) undergoes upon ligand binding are translated to component (b) such that the enzymatic activity can be turned/switched on.

It should be noted that a communication component (c) in accordance with the present disclosure can be, in the simplest case, a single nucleotide which links the aptamer component to the ribozyme component. In one embodiment, where the aptamer component is a stretch of nucleotides which is incorporated into the ribozyme component, i.e. is flanked by parts of the ribozyme component on either side, the communication component is a stretch of nucleotide(s) that links the aptamer component at both its ends to the ribozyme component. Again, the communication component may be a single nucleotide at either end of the aptamer component, in such a case, or it may be a stretch of nucleotides at either end of the aptamer.

It should be noted that that component (c), in some embodiments, introduces flexibility into the aptazyme sensor device, in that it translates conformational changes from component (a) to component (b).

Component (c) preferably comprises RNA, DNA, or combinations thereof.

Components (a), (b) and (c) are covalently bound. It should be noted that an aptazyme sensor device in accordance with the present disclosure also encompasses embodiments, wherein an aptamer component (a) is incorporated into and flanked by a ribozyme component (b). In such an embodiment, the communication component flanks the aptamer component at its both ends and links these both ends to the ribozyme component. In other embodiments, the aptamer component is linked to the ribozyme component only at one end and is not incorporated into the ribozyme component. In such an embodiment, the order of components is (a), (c), (b) or (b), (c), (a). In the embodiments where the aptamer component is incorporated into and flanked by the ribozyme component, the order of components may be (b), (c'), (a), (c"), (b), or (a), (c'), (b), (c"), (a), with (c') and (c") being parts of component (c) and making up component (c), or it may be (b'), (c'), (a), (c"), (b"), or (a'), (c'), (b), (c"), (a"), with (b') and (b") being parts of component (b) and making up component (b), and with (a) and (a") being parts of component (a) and making up component (a).

Substrate or Signalling Molecule

Preferably, the aptazyme sensor device further comprises a substrate.

The substrate is specific for component (b), i.e. the ribozyme with its substrate binding site and enzymatic activity.

The substrate comprises a cleavage site recognized by the ribozyme (i.e. component (b)), preferably one such ribozyme cleavage site. The ribozyme, thus, is capable of catalyzing cleavage of the substrate at the cleavage site.

The substrate preferably comprises a label, such as a fluorescent label, a luminescent label, UV/Vis emitting or absorbing dye, a paramagnetic particle, a paramagnetic particle having a fluorescent label attached, an electrochemical label, preferably fluorescent label.

The substrate is more preferably a molecular beacon or a scorpion primer including a probe or an aptazyme or riboswitch.

As used herein, the term "scorpion primer including a probe" refers to an oligonucleotide which has a secondary structure having a self-complementary shaft region and having at one end a label and at the other end a quencher. Additionally, such scorpion primer includes a primer sequence for use in PCR. A molecular beacon, as used herein, refers to an oligonucleotide which has, at one end a label, such as a fluorescent label, and at the other end a quencher. Typically, the molecular beacon comprises a self-complementary shaft region such that the molecular beacon can form a stem loop. Because of the close vicinity between the quencher and the label, the signal from the label is quenched. If the molecular beacon anneals to another sequence at its loop region, the distance between the quencher and the label increases, and hence, the signal is no longer quenched and can be detected. The same principle also works for the scorpion primers. An "aptazyme" is the combination of an aptamer with a ribozyme, thus combining specific binding to a target molecule (from the aptamer) and the catalytic activity (from the ribozyme). A "riboswitch", as used herein, is meant to refer to an RNA sequence (e.g. as part of an mRNA molecule), which sequence can directly bind to a small target molecule, wherein preferably the binding of the target molecule affects the gene-activity or gene-expression.

As labels for the substrate, various possibilities as outlined above are envisaged. Apart from fluorescent labels, luminescent labels or UV/Vis-emitting or absorbing dyes, also paramagnetic particles are envisaged which can be detected upon application of a rotating unidirection or magnetic field. Under these circumstances, such paramagnetic particles form magnetic chains which rotate with the same frequency as the field. Also combinations of any of the foregoing labels are envisaged.

In any case, signal detection occurs once the substrate has been cleaved, which is only possible, if a ligand has previously bound to the aptamer component.

Aptazyme Sensor Devices with Inhibitory Component (d)

An aptazyme sensor device according to one embodiment of the disclosure furthermore comprises an inhibitory component (d).

Component (d) comprises a single nucleotide strand which is covalently bound to a metal nanoparticle.

The single nucleotide strand of component (d) specifically and selectively binds to the substrate binding site of component (b) such that the enzymatic activity is inhibited, when it is bound.

The single nucleotide strand of component (d) does not contain any cleavage site for the ribozyme (component (b)).

The binding of the single nucleotide strand of inhibitory component (d) to the substrate binding site of component (b) is preferably competitive. The binding of the single nucleotide strand of inhibitory component (d) to the substrate binding site of component (b) is stable at room temperature, in the sense that it remains hybridized to the substrate binding site of component (b) at room temperature. Upon raising the temperature, however, the binding becomes unstable, and the complex "melts", as a result of which the single nucleotide strand dissociates from the substrate binding site. Such elevated temperature can be achieved by general heating or, preferably upon irradiation with light which, in turn, leads to local heating, either directly, or through the excitation of plasmon resonance of the metal nanoparticle which is covalently bound to the single nucleotides strand.

In one embodiment, the binding of the single nucleotide strand to the substrate binding site of component (b) can be selectively interrupted after exciting plasmon resonance of the metal nanoparticle by irradiation of said metal nanoparticle with light.

In one embodiment, the enzymatic activity of component (b) of the aptazyme sensor device is turned/switched on when
 (i) a ligand is bound to component (a) and
 (ii) the inhibitory component (d) is not bound to component (b).

The single nucleotide strand of inhibitory component (d) comprises RNA, DNA, linker molecules, such as PEG, silanes, or combinations thereof.

The metal nanoparticle of inhibitory component (d) is preferably selected from gold, silver, palladium, copper, iron, nickel, titanium, bimetallic core-shell or heterodyne nanoparticles.

The metal nanoparticle can be bound to a solid support, such as glass, membranes, (hydro)gels, porous layers, functionalized glass, filters, nanogaps, or the metal nanoparticle can be a free nanoparticle, in the sense that it is not bound to a solid support but is, for example, free in solution and may, for example, diffuse (with its single nucleotide strand attached).

Aptazyme Sensor Devices with Inhibitory and Signalling Component (e)

Instead of component (d), an aptazyme sensor device according to one embodiment of the disclosure can furthermore comprise an inhibitory and signalling component (e).

In one embodiment, component (e) comprises a single nucleotide strand which has covalently bound a metal nanoparticle and a label.

The metal nanoparticle is preferably bound/attached near or at the 5' end of the single nucleotide strand and the label is preferably bound/attached near or at the 3' end of the single nucleotide strand, or vice versa.

The term "near the 5' end", as used herein, is meant to refer to a scenario, where the binding of the metal nanoparticle occurs within the first 50 nucleotides, preferably the first 40 nucleotides, preferably the first 30 nucleotides, more preferably the first 20 nucleotides, and even more preferably the first 10 nucleotides at the 5' end of the single nucleotide strand. The same remarks also apply to the 3' end. "At the 5' end/3' end" refers to the respective terminal nucleotide.

The single nucleotide strand of component (e) binds to the substrate binding site of component (b) such that the enzymatic activity is inhibited, when it is bound.

The single nucleotide strand has a cleavage site recognized by the ribozyme (i.e. component (b)), preferably one such ribozyme cleavage site. The ribozyme, thus, is capable of catalyzing cleavage of the single nucleotide strand at the cleavage site.

When component (e) is intact, i.e. not cleaved, and bound to component (b) no signal is generated from the label.

The binding of the single nucleotide strand of inhibitory and signalling component (e) to the substrate binding site of component (b) is preferably competitive. The binding of the single nucleotide strand of inhibitory component (d) to the substrate binding site of component (b) is stable at room temperature, in the sense that it remains hybridized to the substrate binding site of component (b) at room temperature. Upon raising the temperature, however, the binding becomes unstable, and the complex "melts", as a result of which the single nucleotide strand dissociates from the substrate binding site. Such elevated temperature can be achieved by general heating or, preferably upon irradiation with light which, in turn, leads to local heating, either directly, or through the excitation of plasmon resonance of the metal nanoparticle which is covalently bound to the single nucleotides strand.

After binding of the ligand to component (a) the enzymatic activity of component (b) is turned on and results in cleavage of the single nucleotide strand of component (e) at the cleavage site. This cleavage of component (e) does not generate a signal from the label.

The binding of component (e) to component (b) as well as of the cleaved component (e) can be selectively interrupted after exciting plasmon resonance of the metal nanoparticle by irradiation with light.

After said interruption of the binding of the cleaved component (e), the signal is generated from the label.

The single nucleotide strand of inhibitory component (d) comprises RNA, DNA, linker, molecules, such as PEG, silanes or combinations thereof.

The metal nanoparticle of inhibitory component (d) is preferably selected from gold, silver, palladium, copper, iron, nickel, titanium, bimetallic core-shell or heterodyne nanoparticles.

The metal nanoparticle can be bound to a solid support, such as glass, membranes, (hydro)gels, porous layers, functionalized glass, filters, nanogaps, or the metal nanoparticle can be a free nanoparticle, in the sense that it is not bound to a solid support but is, for example, free in solution and may, for example, diffuse (with its single nucleotide strand attached).

The label is preferably selected from fluorescent labels, luminescent label, UV/Vis absorbing or emitting dyes, paramagnetic particles, paramagnetic particles having a fluorescent label attached, electrochemical labels, preferably fluorescent labels.

Aptazyme Sensor Devices with Modified Component (a)

In an embodiment of the disclosure, component (a) comprises chemical functionalities, e.g., oligoethylene side chains, carbohydrate chains, zwitterionic molecules, carboxy groups, amino groups, sulfide groups.

In one embodiment, component (a) preferably comprises modified bases or nucleotides which comprise additional amino and/or carboxy and/or sulfide groups allowing reacting with carboxy groups and/or amide groups and/or maleinimide groups.

After synthesis of the aptamer component it is chemically modified in order to reduce its unspecific binding properties. Therefore, bases can be incorporated in the aptamer during synthesis in order to facilitate post-synthetic chemical modification, e.g. additional amino groups to react with carboxygroups, or additional sulfide groups to react with maleinimid groups. The modified bases can be incorporated randomly or rationally. For post-synthetic modification molecules known for low unspecific binding, e.g. oligoethylene-chains of any molecular weight, carbohydrate chains, zwitter-ionic molecules can be coupled to the aptamer, e.g. via carboxy-groups or maleinimid-groups. The post-synthetic modification is chosen such that it will not interfere with the specific recognition of the molecular complexes to be detected.

Arrays of Aptazyme Sensor Devices

As described above, the present disclosure also provides arrays of aptazyme sensor devices.

These arrays of aptazyme sensor devices are in particular suitable for detecting different ligands (analytes) in one reaction vessel.

The arrays of the disclosure comprise different aptazyme sensor devices which comprise the same component (b) but differ in their component (a), i.e. they each comprise a component (a) that binds to a different ligand or analyte, and which differ in their inhibitory component (d) or (e), i.e. they each comprise a component (d) or (e) bound to a different metal nanoparticle, which allows
- parallel detection of several ligands (analytes) in one reaction vessel with a single readout mechanism
- in a time-resolved manner.

Furthermore, these arrays can be combined with spatial separation of reactions and with multiple readout signals and thereby increases the combinatorial possibilities of parallelized sensing.

In one embodiment, an array of aptazyme sensor devices with different inhibitory components (d) is provided.

An array of aptazyme sensor devices for detecting different ligands comprises in one reaction vessel
- (i) a substrate with a label as defined herein,
- (ii) at least two aptazyme sensor devices according to the disclosure,
- wherein each aptazyme sensor device comprises
- a different aptamer component (a) comprising a binding site for a different ligand, and an inhibitory component (d) comprising a different metal nanoparticle.

For each aptazyme sensor device and depending on the metal nanoparticle comprised, the binding of the inhibitory component (d) to component (b) is selectively interrupted by irradiation with light of a specific different wavelength.

In one embodiment, an array of aptazyme sensor devices with different inhibitory and signalling components (e) is provided.

An array of aptazyme sensor devices for detecting different ligands comprises in one reaction vessel
- at least two aptazyme sensor devices according to the disclosure,
- wherein each aptazyme sensor device comprises a different aptamer component (a) comprising a binding site for a different ligand, and an inhibitory and signalling component (e) comprising a different metal nanoparticle.

For each aptazyme sensor device and depending on the metal nanoparticle comprised, the binding of the cleaved component (e) to component (b) is selectively interrupted and signal is generated by irradiation with light of a specific different wavelength.

Preferably, the reaction vessel of an array of the disclosure is selected from a tube, a plate, a membrane, vessel, a slide, such as a microscopy slide, a porous material with an interstitial space for accommodating said array of aptazyme sensor devices, such as gels or polymers.

Preferably, the metal nanoparticles are immobilized onto a solid support, such as glass, membranes, (hydro)gels, porous layers, functionalized glass, filters, nanogaps, or are free nanoparticles, e.g. nanoparticles in solution.

Uses of the Aptazyme Sensor Devices and Arrays Thereof

As described above, the present disclosure provides uses of the aptazyme sensor devices according to the disclosure and of the arrays of aptazyme sensor devices according to the disclosure.

An aptazyme sensor device according to the disclosure is provided for the use for detecting a ligand in a sample.

An array of aptazyme sensor devices according to the disclosure is provided for the use for detecting different ligands in a sample.

The sample is preferably selected from whole blood, serum, plasma, urine, saliva, sputum, sweat, breath condensate, tear fluid, sperm fluid, vaginal fluid, food extracts, and environmental samples.

An aptazyme sensor device according to the disclosure, which comprises a modified component (a), as described above, is provided for the use for reducing unspecific binding properties of component (a).

Methods for Detecting Ligands in a Sample

As described above, the present disclosure provides methods for detecting ligand(s) in a sample utilizing the aptazyme sensor devices according to the disclosure or the arrays of aptazyme sensor devices according to the disclosure.

A method of detecting a ligand or analyte in a sample comprises
- (i) providing a sample,
- (ii) providing an aptazyme sensor device according to any of claims 1 to 11 and a substrate with a label as defined in claim 4; or providing an aptazyme sensor device according to any of claims 15 to 18,
- (iii) contacting said sample with said aptazyme sensor device,
- (iv) irradiating the sample with said aptazyme sensor device with light of the wavelength which excites plasmon resonance of the metal nanoparticle of component (d) or (e) of the aptazyme sensor device,
- (v) detecting the signal.

A method of detecting different ligands or analytes in a sample comprises
- (i) providing a sample,
- (ii) providing an array of aptazyme sensor devices according to any of claim 12 to 14 or 18,
- (iii) contacting said sample with said array of aptazyme sensor devices,
- (iv) irradiating the sample with said array of aptazyme sensor devices with light of the wavelength which excites plasmon resonance of one type of metal nanoparticle of component (d) or (e) of the aptazyme sensor devices of said array,
- (v) detecting the signal,
- (vi) repeating steps (iv) and (v) depending on the number of different metal nanoparticles of said array of aptazyme sensor devices.

The sample is preferably selected from whole blood, serum, plasma, urine, saliva, sputum, sweat, breath condensate, tear fluid, sperm fluid, vaginal fluid, food extracts, and environmental samples.

Improvement of Shelf-Life

Aptazyme sensors are known in the art. The working principle of an aptazyme is illustrated in the FIG. 1. The ribozyme (i.e. component (b) of the disclosure) is used for signal generation. Its enzymatic activity leads to signal amplification once the activity is switched "on". Signal is generated by cleaved substrate, e.g. quenched molecular beacon. The aptamer module (i.e. component (a) of the disclosure) switches the enzymatic activity of the ribozyme "on" once ligand (analyte) has bound. In the absence of ligand the aptamer keeps the enzymatic activity "off". The communication module (i.e. component (c) of the disclosure) translates changes in the binding state of the aptamer to changes in enzymatic activity of the ribozyme.

In the ideal aptazyme sensors the enzymatic activity would be zero in absence of the ligand and would be very high in presence of ligand. In real sensors this cannot be achieved together. High enzymatic activity in "on"-state usually leads to residual activity in the "off"-state. And zero activity in the "off"-state usually leads to low activity in the "on"-state.

Particularly problematic is that any residual activity in the "off"-state is detrimental to shelf-life of the sensors and therefore a severe obstacle to commercial application. Residual activity reduces the amount of available signalling substrate, e.g. reducing amount of quenched molecular beacon. Moreover, residual activity increases background signal over time and reduces sensor sensitivity drastically.

Embodiments of the Inventive Solution According to the Present Disclosure

In order to avoid residual activity an additional inhibitor of enzymatic activity is used (i.e. component (d) of the disclosure). The inhibitor is a nucleotide strand that binds competitively to the substrate binding site of the ribozyme and lacks any cleavage site. At room temperature this competitive binding is very stable and efficiently blocks enzymatic activity. Efficient blocking of enzymatic activity allows long shelf-life of aptazyme and signaling molecules (substrate), such as molecular beacons. The competitive strand is covalently bound to metal-nanoparticle to ensure close proximity to this metal nanoparticle. Irradiation of light that excites plasmon resonances in the metal nanoparticle leads to local heating and thus melting of the competitive strand. This melting process releases enzymatic activity and allows aptazyme-sensing as known. Competitive strand and the metal-nanoparticle (i.e. component (d) of the disclosure) are called a "fuse". Local heating induced release of aptazyme can be called "defusing" the aptazyme. Irradiation can be maintained throughout the sensing process to avoid competitive inhibition. (see also FIG. 2).

Advantage of the Inventive Solution

An additional inhibition that can be released directly before the measurement without disturbing the measurement can increase shelf-life and enables commercial use of aptazyme sensors.

Using metal-nanoparticles to heat the sample locally is an advantage compared to heat the sample in bulk because 1) It does not damage heat-sensitive analytes and thus keeps heat sensitive analytes in their native state. This is particularly important when the native state is crucial for their recognition by the aptamer.

2) The enzymatic reaction should occur at controlled temperature. The temperature must be close to room temperature because ribozymal activity is heat sensitive itself. In case of bulk heating the sample must therefore be cooled after defusing the aptazyme. This bulk cooling would allow fusing the aptazyme again. In case of using nanoparticles, the local heating could be maintained and fusing of aptazyme prevented while the enzymatic reaction is running in bulk at controlled temperature.

Using fused aptazymes is an advantage compared to "kit" solutions because of its simplicity for the user. Given the situation that residual activity of the aptazyme is detrimental to the sensing component and shelf-life. An obvious solution would be to keep the components separate until usage and let the user combine the components directly before using them. The present disclosure has nevertheless advantages compared to this obvious solution 1) No additional step in the analytical procedure are required which means less sources of error 2) No training, special skills or particular awareness of error sources is required from the user Parallelization A problem in the art is the limitation of parallelization of a sensor reaction in a single reaction vessel. A situation might be given in which one sensing mechanism (ribozyme+substrate+signal) is coupled to different aptamer modules recognizing different analytes and all possible combinations are pooled in one reaction vessel. In such a situation it would not be possible to tell what analyte led to a given signal. This makes a spatial separation of the reaction or different readout signals necessary. These requirements restrict a parallelized sensor to certain formats.

Embodiments of the Inventive Solution According to the Present Disclosure

The plasmon wavelength of metal nanoparticles depends on particle properties such as type of metal, size, coating or shape. Plasmon resonances of different metal nanoparticles are excited by light of different wavelength. This selective excitation can be used for selective defusing. This selective defusing mechanism allows a time-controlled activation of specific aptazyme which enables the discrimination of different aptazyme-mediated signals in a single reaction vessel when a single readout mechanism is employed.

Two different implementations are illustrated in FIG. 3.

A) Different aptazmyes are blocked by a so called fuse (complementary oligonucleotide with different nanoparticles, i.e. component (d) of the disclosure with different metal nanoparticles). After defusing one selected aptazyme by applying a defined wavelength, the reaction can start. For this the signaling molecule binds to the aptazyme, leading to a signal in the presence of a bound analyte. Due to the selective aptamer, different kind of analytes bind to different aptazmyes with different fuse. The whole system needs only one type of signaling molecule (e.g. molecular beacon). The signaling process is therefore initiated by applying a specific wavelength in the presence of an analyte. This means various analytes can be deteced timeresolved in one reaction vessel. As after signaling the aptazyme can be refused by switching off the specific wavelength this sensor can be considered as a re-use sensor.

B) In the second implementation, the fuse consists of the nanoparticles and the signaling molecule (i.e. signalling and inhibitory component (e) of the disclosure). As in case A) different analytes can bind to different aptazymes and corresponding fuse. After applying a specific wavelength the signal is generated by the release of the fuse (nanoparticle and signaling molecule) when an analyte is bound. As the signaling molecule is already attached to the aptazyme, this sensor is considered to be a single-use disposable sensor.

In both cases the complexes can be either in solution or the metal-nanoparticles could also be immobilized onto a solid support.

Advantage of the Present Disclosure

An advantage of the disclosure is that it offers an additional element of controlling the sensor specificity that has not been described before. With following advantages over state-of-the-art:

1) This allows the parallel detection of several analytes in one reaction vessel with a single readout mechanism that was not possible before.

2) It can be combined with spatial separation of reactions and with multiple readout signals and thereby increases the combinatorial possibilities of parallelized sensing.

Unspecific Binding

Aptamers can be used as probes for an analyte. Thereby the analyte is immobilized to a surface by a capture molecule, e.g. a second aptamer or an antibody, forming a surface bound molecular complex. The first aptamer is used as a probe to make this molecular complex visible. It is necessary for the aptamer probe to 1) recognize specifically the surface bound molecular complex 2) carry a detectable label, e.g a fluorophor, radioactive isotope, enzyme 3) absence of unspecific binding to surface.

Aptamer probes binding unspecifically to surfaces is a widespread problem and reduces sensor performance by leading to false positive results and decreasing sensor sensitivity. A common solution to this problem is to modify the surface chemically, e.g. with oligoethylene-chains, such that the surface is rendered "non-binding".

Embodiments of the Inventive Solution According to the Present Disclosure

After synthesis of the aptamer probe it is chemically modified in order to reduce its unspecific binding properties. Therefore, bases can be incorporated in the aptamer during synthesis in order to facilitate post-synthetic chemical modification, e.g. additional amino groups to react with carboxy-groups, or additional sulfide groups to react with maleinimid groups. The modified bases can be incorporated randomly or rationally. For post-synthetic modification molecules known for low unspecific binding, e.g. oligoethylen-chains of any molecular weight, carbohydrate chains, zwitter-ionic molecules can be coupled to the aptamer, e.g. via carboxy-groups or maleinimid-groups. The post-synthetic modification is chosen such that it will not interfere with the specific recognition of the molecular complexes to be detected.

Advantage of the Present Disclosure

The solution provides a method to avoid unspecific binding in addition to common surface modification strategies. This is particularly an advantage when surface modification is not possible or not available. Post-synthetic modification of aptamers is independent of the sensor surface used and not affected by restrictions coming along with surface chemistries. For example, when sensitive capture agent such as an antibody is bound to the surface, then "harsh" conditions like high temperatures or organic solvents cannot be applied anymore to modify the surface efficiently.

Sometimes "non-binding" surfaces become "binding" after initial contact with a complex sample like whole blood or serum. This is because sensor surface is large on a molecular scale and thus some molecules, e.g. proteins, bind to even non-binding and render them locally "binding". The surface of the aptamer is small on a molecular scale and thus the rare binding event of a molecule to a "non-binding" surface can be neglected.

The following drawings illustrate the present disclosure without, however, limiting the same thereto.

Figure 1:
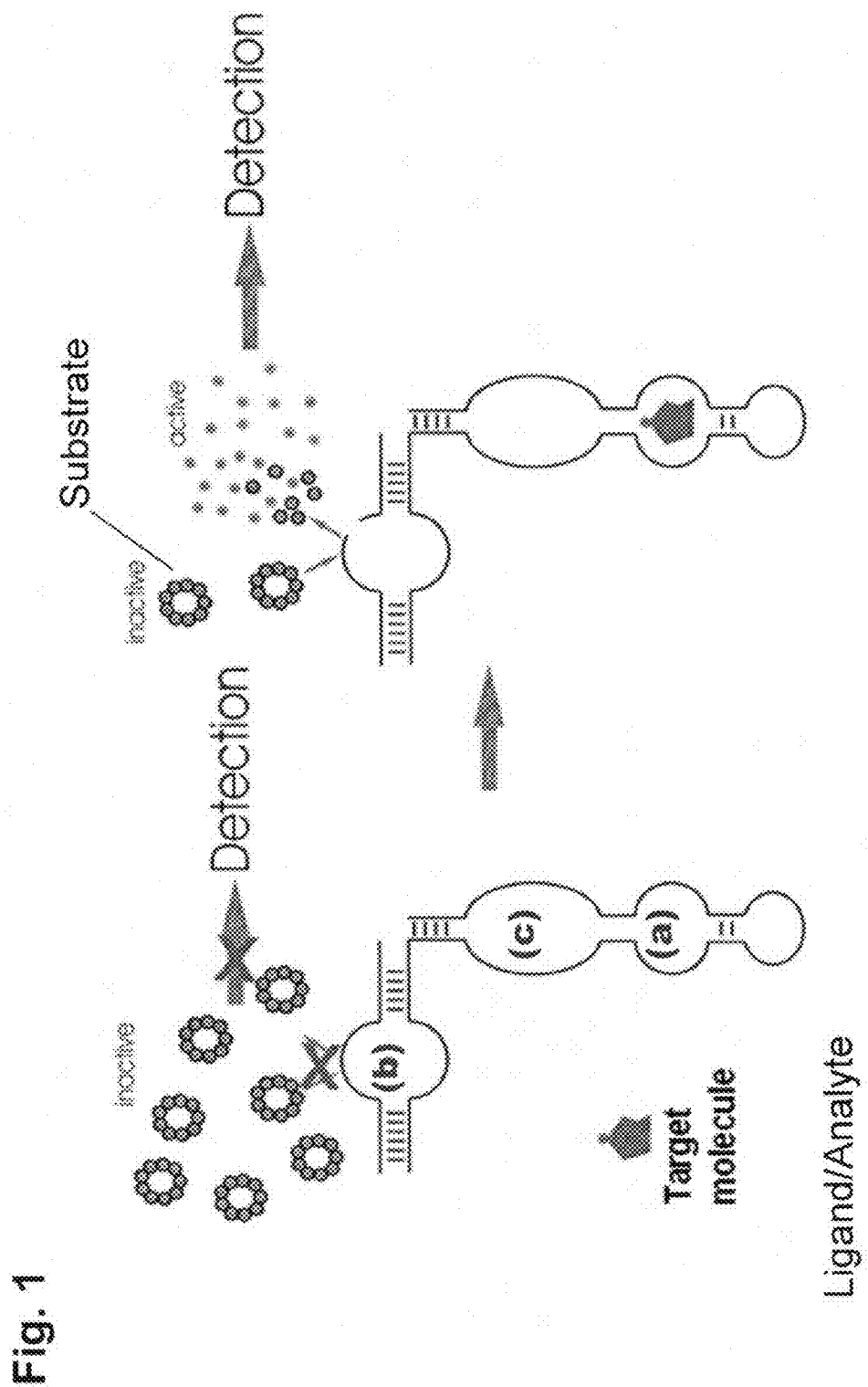
FIG. 1 Working Principle of Aptazyme Sensors.

The working principle of an aptazyme is illustrated in FIG. 1. Three components of the aptazyme are necessary: a) the aptamer ligand binding module (component (a) of the disclosure), b) the enzymatic ribozyme module (component (b) of the disclosure), c) communication module (component (c) of the disclosure).

FIG. 2 Aptazyme Sensor Device According to the Disclosure with Nanoparticle Fuse (i.e. Inhibitory Component (d)).

The working principle of an aptazyme sensor device with nanoparticle fuse (component (d)) is shown. When the nanoparticle fuse is bound, no cleavage of the substrate (a molecular beacon) occurs due to residual activity. By local radiative heating, the nanoparticle fuse is defused (binding of component (d) is interrupted), such that binding of the ligand to the aptamer component results in enzymatic activity of the ribozyme component, resulting in cleavage of the molecular beacon substrate and, thus, a signal. Binding of the substrate to the substrate binding site may occur with or without ligand being present or bound.

Figure 3B:
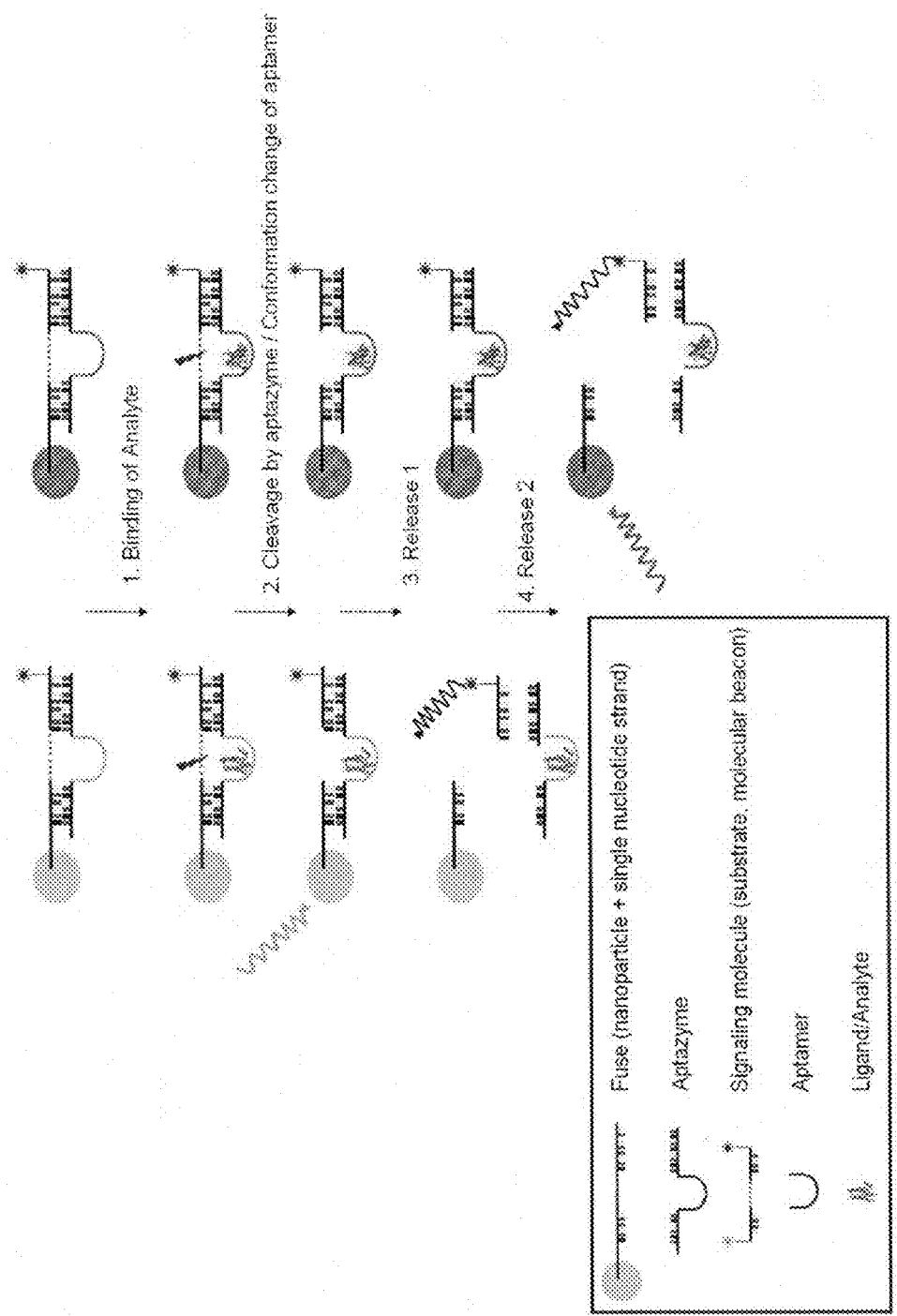

FIG. 3 Multianalyte Analysis According to the Disclosure. (A) Using an array of aptazyme sensor devices as shown in FIG. 2.

(B) Using an array of another aptazyme sensor devices according to the disclosure, utilizing an inhibitory and signalling component (e).

The present application claims priority of EP patent application No. 12 180 409.0 filed on 14 Aug. 2012, the entire contents of which are incorporated herein by reference.

The invention claimed is:

1. An aptazyme sensor device for detecting a ligand, said device comprising the following three components
   (a) an aptamer component, which comprises a binding site for a ligand,
   (b) a ribozyme component having a substrate binding site, wherein said ribozyme component has an enzymatic activity towards a substrate, which enzymatic activity can be switched on and off, and which, if switched on, results in generation of a detectable signal upon exposure of the ribozyme component to the substrate and upon binding of the substrate to the substrate binding site,
   (c) a communication component, which is a single or double stranded nucleic acid and links (a) to (b) and translates changes in the binding state of component (a) to component (b),
   wherein (a), (b) and (c) are covalently bound in the order of (a), (c), (b) and/or in the order of (b), (c), (a), or combinations thereof selected from (b), (c), (a), (c), (b), or (a), (c), (b), (c), (a),
furthermore comprising
   (d) an inhibitory component, which comprises a single nucleotide strand covalently bound to a metal nanoparticle, wherein the single nucleotide strand specifically and selectively binds to the substrate binding site of component (b) such that the enzymatic activity in (b) is inhibited,
   wherein binding of the single nucleotide strand to the substrate binding site of component (b) is selectively interrupted after exciting plasmon resonance of the metal nanoparticle by irradiation of said metal nanoparticle with light, wherein the enzymatic activity of component (b) is switched on when
    (i) a ligand is bound to component (a) and
    (ii) the inhibitory component (d) is not bound to component (b).
2. The aptazyme sensor device of claim 1, wherein component (a) comprises RNA, DNA, or combinations thereof.
3. The aptamer sensor device of claim 1 wherein component (a) is incorporated in component (b) and is flanked at either end by parts of components (c) and (b).
4. The aptazyme sensor device according to claim 1, furthermore comprising a substrate.
5. The aptazyme sensor device of claim 4, wherein the signal caused by said ribozyme component (b) results from the enzymatic activity of component (b) causing a change causing the occurrence of said signal or of an increase in said signal.
6. The aptazyme sensor device of claim 1, wherein binding of the single nucleotide strand of inhibitory component (d) to the substrate binding site (of component (b)) is competitive.
7. The aptazyme sensor device of claim 1, wherein the single nucleotide strand of inhibitory component (d) comprises RNA, DNA, linker molecules, such as PEG, silanes, or combinations thereof.
8. The aptazyme sensor device of claim 1, wherein the metal nanoparticle of inhibitory component (d) is selected from gold, silver, palladium, copper, iron, nickel, titanium, bimetallic core-shell or heterodyne nanoparticles.
9. The aptazyme sensor device of claim 1, wherein component (c) comprises RNA, DNA, or combinations thereof, and wherein component (c) may occur several times within said aptazyme sensor device, e.g. if (a) is incorporated into (b) and is flanked by parts of (b) on either side.
10. The aptazyme sensor device of claim 1, wherein component (a) comprises a chemical functionality.
11. The aptazyme sensor device of claim 9, wherein component (a) comprises modified bases/nucleotides which comprise additional amino and/or carboxy and/or sulfide groups allowing reacting with carboxy groups and/or amine groups and/or maleinimide groups.
12. An array of aptazyme sensor devices for detecting different ligands comprising in one reaction vessel
    (i) a substrate with a label,
    (ii) at least two aptazyme sensor devices as defined in claim 1,
    wherein each aptazyme sensor device comprises
    a different aptamer component (a) comprising a binding site for a different ligand, and
    an inhibitory component (d) comprising a different metal nanoparticle,
such that, for each aptazyme sensor device and depending on the metal nanoparticle comprised, the binding of the inhibitory component (d) (to component (b)) is selectively interrupted by irradiation with light of a specific different wavelength.
13. The array of claim 12, wherein the reaction vessel is selected from a tube, a plate, a membrane, vessel, a slide, and a porous material with an interstitial space for accommodating said array of aptazyme sensor devices.
14. The array of claim 12, wherein the metal nanoparticles are immobilized onto a solid supportor are free nanoparticles in solution.
15. An aptazyme sensor device comprising the following three components
    (a) an aptamer component, which comprises a binding site for a ligand,
    (b) a ribozyme component having a substrate binding site, wherein said ribozyme component has an enzymatic activity towards a substrate which enzymatic activity can be switched on and off,
    (c) a communication component, which is a single or double stranded nucleic acid and translates changes in the binding state of component (a) to component (b),
    wherein (a), (b) and (c) are covalently bound in the order of (a), (c), (b) and/or in the order of (b), (c), (a), or combinations thereof selected from (b), (c), (a), (c), (b), or (a), (c), (b), (c), (a),
furthermore comprising
    (e) an inhibitory and signalling component, which comprises a single nucleotide strand having a ribozyme cleavage site and which has covalently bound a metal nanoparticle near or at the 5' end and a label near or at the 3' end yes or vice versa, wherein the single nucleotide strand binds to the substrate binding site of component (b) such that the enzymatic activity is inhibited,
    wherein after binding of the ligand to component (a) the enzymatic activity of component (b) is switched on and results in cleavage of the single nucleotide strand of component (e) at the cleavage site, but wherein no detectable signal is generated from the label,
    and wherein, after exciting plasmon resonance of the metal nanoparticle by irradiation with light, binding of the cleaved component (e) to component (b) is selectively interrupted such that the detectable signal is generated from the label.
16. The aptazyme sensor device of claim 15, wherein component (a) comprises RNA, DNA, or combinations thereof.
17. The aptazyme sensor device of claim 15, wherein the label is selected from fluorescent labels, luminescent labels, UV Vis emitting or absorbing dyes, paramagnetic particles, paramagnetic particles having a fluorescent label attached, electrochemical labels, preferably fluorescent labels.
18. The aptazyme sensor device of any of claim 15, wherein the single nucleotide strand of inhibitory component (e), the metal nanoparticle of inhibitory component (e), component (c) and component (a) comprises RNA, DNA, linker molecules, such as PEG, silanes, or combinations thereof.
19. A method of detecting a ligand in a sample comprising
    (i) providing a sample,
    (ii) providing an aptazyme sensor device according to claim 1 and a substrate with a label,
    (iii) contacting said sample with said aptazyme sensor device,
    (iv) irradiating the sample with said aptazyme sensor device with light of the wavelength which excites plasmon resonance of the metal nanoparticle of component (d) or (e) of the aptazyme sensor device,
    (v) detecting a signal.
20. A method of detecting different ligands in a sample comprising
    (i) providing a sample,
    (ii) providing an array of aptazyme sensor devices according to claim 12,
    (iii) contacting said sample with said array of aptazyme sensor devices,
    (iv) irradiating the sample with said array of aptazyme sensor devices with light of the wavelength which excites plasmon resonance of one type of metal nanoparticle of component (d) or (e) of the aptazyme sensor devices of said array,
    (v) detecting a signal, (vi) repeating steps (iv) and (v) depending on the number of different metal nanoparticles of said array of aptazyme sensor devices.

21. The aptazyme sensor device according to claim 4, wherein said substrate is labelled.

22. The aptazyme sensor device according to claim 4, wherein said substrate is a molecular beacon or a scorpion primer, including a probe, or an aptazyme or riboswitch.

23. The aptazyme sensor device according to claim 4, wherein said change is the result of cleavage of the substrate.

24. The aptazyme sensor device according to claim 10, wherein said chemical functionality is selected from the group consisting of an oligoethylene side chain, a carbohydrate chain, a zwitterionic molecule, a carboxy group, an amino group, and a sulfide group.

25. A method of detecting a ligand in a sample comprising
(i) providing a sample,
(ii) providing an aptazyme sensor device according to any of claims 15,
(iii) contacting said sample with said aptazyme sensor device,
(iv) irradiating the sample with said aptazyme sensor device with light of the wavelength which excites plasmon resonance of the metal nanoparticle of component (d) or (e) of the aptazyme sensor device,
(v) detecting a signal.

\* \* \* \* \*